(12) United States Patent
Wakefield et al.

(10) Patent No.: US 11,635,354 B2
(45) Date of Patent: Apr. 25, 2023

(54) SPATIAL MOLECULAR PROFILING OF SOLID BIOLOGICAL MASSES AND PROFILE STORAGE

(71) Applicant: Global Life Sciences Solutions Operations UK Ltd, Sheffield (GB)

(72) Inventors: Alison Myfanwy Wakefield, Cardiff (GB); Jeffrey Kenneth Horton, Cardiff (GB); Peter James Tatnell, Cardiff (GB)

(73) Assignee: Global Life Sciences Solutions Operations UK Ltd, Sheffield (GB)

( * ) Notice: Subject to any disclaimer, the term of this patent is extended or adjusted under 35 U.S.C. 154(b) by 568 days.

(21) Appl. No.: 15/318,297

(22) PCT Filed: Jun. 23, 2015

(86) PCT No.: PCT/EP2015/064037
§ 371 (c)(1),
(2) Date: Dec. 12, 2016

(87) PCT Pub. No.: WO2016/001006
PCT Pub. Date: Jan. 7, 2016

(65) Prior Publication Data
US 2017/0131188 A1 May 11, 2017

(30) Foreign Application Priority Data
Jun. 30, 2014 (GB) .................................. 1411624.8

(51) Int. Cl.
*G01N 21/00* (2006.01)
*G01N 1/28* (2006.01)
(Continued)

(52) U.S. Cl.
CPC ............ *G01N 1/2813* (2013.01); *B01L 3/508* (2013.01); *C12Q 1/6806* (2013.01); *C12Q 1/686* (2013.01);
(Continued)

(58) Field of Classification Search
CPC .......................... G01N 21/6428; G01N 21/79
(Continued)

(56) References Cited

U.S. PATENT DOCUMENTS

| 2001/0050810 | A1* | 12/2001 | Lorincz ..... G01N 1/30 359/396 |
| 2004/0081979 | A1* | 4/2004 | Knezevic ..... B01L 3/5023 435/6.14 |
| 2015/0252356 | A1 | 9/2015 | Park et al. |

FOREIGN PATENT DOCUMENTS

| JP | 2007-175046 A | 7/2007 |
| JP | 2010-256369 A | 11/2010 |

(Continued)

OTHER PUBLICATIONS

European Office Action for EP Application No. 15731561.5 dated Feb. 12, 2018 (6 pages).
(Continued)

*Primary Examiner* — Natalia Levkovich
(74) *Attorney, Agent, or Firm* — Eversheds Sutherland (US) LLP (57) ABSTRACT

Disclosed is a method for capturing the spatial molecular profiling of a biological mass formed from biological material, comprising the steps of: a) providing a transected biological mass, for example a tumour, the transection exposing at least a portion of the mass; b) providing a solid support of an area at least equalling the area of said portion of the mass; c) transferring biological material from the portion of the mass to the support to provide on the support (Continued)

a two dimensional imprint of the biological material present at the portion of the mass; and d) performing a biological assay of the transferred biological material from different predetermined locations of the imprint in order to determine the spatial molecular profile of the portion of the mass.

8 Claims, 6 Drawing Sheets

Specification includes a Sequence Listing.

(51) Int. Cl.
| | |
|---|---|
| *C12Q 1/6806* | (2018.01) |
| *C12Q 1/6841* | (2018.01) |
| *G01N 33/574* | (2006.01) |
| *B01L 3/00* | (2006.01) |
| *C12Q 1/686* | (2018.01) |

(52) U.S. Cl.
CPC ......... *C12Q 1/6841* (2013.01); *G01N 33/574* (2013.01); *B01L 2200/16* (2013.01); *G01N 2001/282* (2013.01)

(58) Field of Classification Search
USPC .................................................. 436/172, 169
See application file for complete search history.

(56) References Cited

FOREIGN PATENT DOCUMENTS

| WO | 2002/048674 A2 | 6/2002 |
|---|---|---|
| WO | 2010/088517 A1 | 8/2010 |
| WO | 2012/140224 A1 | 10/2012 |
| WO | 2014/060483 A1 | 4/2014 |
| WO | 2014/072354 A1 | 5/2014 |

OTHER PUBLICATIONS

Egualuz et al, "Multitissue array review: a chronological description of tissue array techniques, applications and procedures", Pathology, Research and Practice, vol. 202, No. 8, Jan. 1, 2006, 8 pages.

International Search Report and Written Opinion regarding International Application No. PCTP/EP2015/064037, dated Sep. 28, 2015, 13 pages.

GB Search Report regarding GB Application No. 1411624.8, dated Mar. 10, 2015, 5 pages.

Roh et al., "Tissue imprint for molecular mapping of deep surgical margins in patients with head and neck squamous cell carcinoma", Head & Neck, vol. 34, issue 11, Nov. 2012, pp. 1529-1536.

Bigras et al., "Spatial distribution of DNA ploidy in colorectal carcinoma", Analytical Cell Pathology, vol. 7, issue 4, 1994, pp. 289-300.

Buno et al., "Lymphoma associated chromosomal abnormalities can easily be detected by FISH on tissue imprints. An Underused Diagnostic Alternative", Journal of Clinical Pathology, vol. 58, 2005, 5 pgs.

Goldstein et al., "Studies on fluorescent antibody staining: I. Non-specific fluorescence with fluorescence-coupled sheep anti-rabbit globulins", Journal of Experimental Medicine, vol. 114, issue 1, 1961, 23 pages.

Modern Biology, Inc., Tissue Printing (IND-2), retrieved from http://www.modernbio.com/experiment/tissue-printing, publicly available at least by Mar. 10, 2015, 5 pages.

Petras et al., "KRAS detection in colonic tumours by DNA extraction from FTA paper: The Molecular Touch-Prep", Diagnostic and Molecular Pathology, vol. 20, issue 4, 2011, p. 189-193.

Japanese Office Action for JP Application No. 2016-575441 dated Jul. 23, 2019 (9 pages, English translation).

Chinese Office Action for CN Application No. 201580035647.9 dated Mar. 3, 2020 (27 pages with English translation).

Japanese Office Action for JP Application No. 2016-575441 dated Mar. 23, 2020 (9 pages with English translation).

Saieg et al., "The Use of FTA Cards for Preserving Unfixed Cytological Material for High-Throughput Molecular Analysis," Cancer Cytopathology, 2012, 120:206-214.

\* cited by examiner

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: eNOS exon 10-specific forward primer

<400> SEQUENCE: 1
atttcctgtc ccctgccttc                                              20

<210> SEQ ID NO 2
<211> LENGTH: 20
<212> TYPE: DNA
<213> ORGANISM: Artificial Sequence
<220> FEATURE:
<223> OTHER INFORMATION: eNOS Neo-specific forward primer

<400> SEQUENCE: 2
ttgctacccg tgatattgct                                              20

<210> SEQ ID NO 3
<211> LENGTH: 20
<212> TYPE: DNA
<213> ORGANISM: Artificial Sequence
```

-continued

```
<220> FEATURE:
<223> OTHER INFORMATION: eNOS exon 12-specific reverse primer

<400> SEQUENCE: 3
ggccagtctc agagccatac                                                 20
```

SPATIAL MOLECULAR PROFILING OF SOLID BIOLOGICAL MASSES AND PROFILE STORAGE

FIELD OF THE INVENTION

This invention relates to ex vivo spatial molecular profiling of biological masses such as tumours and the storage of such a profile.

BACKGROUND OF THE INVENTION

Herein 'spatial molecular profiling' refers to the determination of the composition of biological material at a molecular, or macro-molecular level. Herein macro-molecular includes genomic, RNA expression, proteomic and enzymatic information. The inventors consider that spatial molecular profiling of biological tumours as well as other biological masses, such as cellular formations, is essential for determining patterns of gene and protein expression that result in the biological changes which characterise different cell types for example in solid tumours, for example, but not limited to, breast, lung, prostate and colorectal cancers. Molecular profiling of tumours, however, is greatly complicated by the intrinsic biological heterogeneity of tumours. There is an increasing need for technologies that allow the analysis of multiple biomarkers in 'a spatial-molecular map' across both the tumour and the surrounding extracellular matrix. In embodiments, this invention will enable the identification of tumour region-specific gene expression and gene rearrangement profiles, and protein expression profiles, which will provide vital information on tumour heterogeneity and will facilitate treatment and clinical decisions, prognosis predictions and fundamental tumour biology research.

Molecular profiling of malignant tumours is essential for determining appropriate tumour-specific treatment regimens and for predicting prognosis. Of particular importance is the analysis of molecular markers that characterize invasive tumours as, very often, mortality from cancer does not result from the primary tumour, but from secondary tumours (metastases) that arise in other organs. Such molecular markers include those that are involved in epithelial-to-mesenchymal transition (EMT), a process which results in non-invasive epithelial cells gaining a more mesenchymal phenotype and therefore becoming increasingly invasive in their behaviour.

Currently, methods for molecular profiling of tumours include microarray analysis of the expression of large numbers of genes from bulk tumour samples which can be expensive and time consuming.

Molecular profiling is further complicated by the fact that tumours have inherent biological heterogeneity and therefore very different gene expression profiles are present depending on which part of the bulk sample is taken. Currently, in both clinical and research settings, bulk tumour samples are stored in formalin fixed paraffin embedded (FFPE) blocks. This storage method is not widely adopted because nucleic acid isolated from these blocks is usually degraded and contains more PCR inhibitors than nucleic acid isolated from non-fixed tissue. Additionally, the physical space needed for storage of a large number of specimens is often not available. Furthermore, specific gene expression patterns across the tumour cannot always be analysed easily as the 2-dimensional (2D) tumour structure may be lost. This is especially problematic when attempting to analyze molecular markers of invasion such as those involved in EMT, which are predominantly differentially expressed only at the edge, or invasive front, of the tumour (Kahlert C, Lahes S et al. Overexpression of ZEB2 at the invasion front of colorectal cancer is an independent prognostic marker and regulates tumour invasion in vitro. Clin. Cancer Res. 2011; 17, 24:7654-7663.; Usami Y, Satake S et al. Snail-associated epithelial-mesenchymal transition promotes oesophageal squamous cell carcinoma motility and progression. J Pathol. 2008; 215,3,330-339.).

A previous study examined the use of a solid support paper sold under the trade name FTA® for collection and isolation of DNA collected from colorectal tumour samples for use in real-time PCR-based KRAS assays (Petras M L, Lefferts J A et al. KRAS detection in colonic tumours by DNA extraction from FTA Paper: The molecular touch-prep. Diagn Mol Pathol. 2011; 20,4:189-193). DNA from colonic tumours was collected by taking a slice through the tumour before applying FTA paper directly to the cut surface. KRAS mutation analysis was carried out on DNA extracted from these samples and from matched FFPE blocks. Results demonstrated 100% correlation between the two DNA collection methods and highlighted the feasibility of using a paper support to successfully store tumour samples for future nucleic acid isolation and downstream analysis. However, only one genomic mutation was analysed and the study did not perform two dimensional tumour gene expression profiles or consider other analytes such as enzymes.

In light of this background, there is a need for a high quality nucleic acid, protein and enzyme storage system that enables the 2D tumour structure to be interrogated, potentially after a period of storage in a 'bank' or the like, thereby allowing spatially relevant downstream gene expression analysis etc, to take place.

The inventors have realised the requirement for a tumour molecular profiling method & kit that will allow the transfer of tumour cells and other biomarkers such as mRNA and proteins, including enzymatic proteins, from the tissue surface directly onto a suitable solid support for storage in its original 2D spatial context, for example using a detergent treated paper such as FTA, allowing long term storage.

When required, samples for example samples punched from the paper, can then be taken from any area of the tumour imprinted paper support for downstream molecular analysis that is specific to that area of the tumour.

The invention provides a method according to claim 1 having preferred features defined by claims dependent on claim 1.

The invention provides also apparatus as defined by claim having preferred features defined in claims dependent thereon.

The invention extends to a kit which includes a dried reagent set for example in the form of readily useable beads that contain primers to analyse specific gene expression signatures. The method will be particularly useful in identifying the differential expression of invasion-related genes that are often only differentially expressed at the invasive front of the tumour and so are not identified in bulk tumour analysis. The kit could be utilised in both the analysis of clinical samples and in pre-clinical tumour biology research.

This invention extends to protein expression profiling using untreated paper and downstream protein based assays, and this disclosure has not been previously reported elsewhere. The invention will encompass product, method and kit claims.

The invention extends to any combination of features disclosed herein, whether or not such a combination is mentioned explicitly herein. Further, where two or more features are mentioned in combination, it is intended that such features may be claimed separately without extending the scope of the invention.

BRIEF DESCRIPTION OF THE DRAWINGS

The invention can be put into effect in numerous ways, illustrative embodiments of which are described below with reference to the drawings, wherein.

DETAILED DESCRIPTION OF THE INVENTION

The invention, together with its objects and the advantages thereof, may be understood better by reference to the following description taken in conjunction with the accompanying drawings, in which like reference numerals identify like elements in the Figures.

Figure 1:
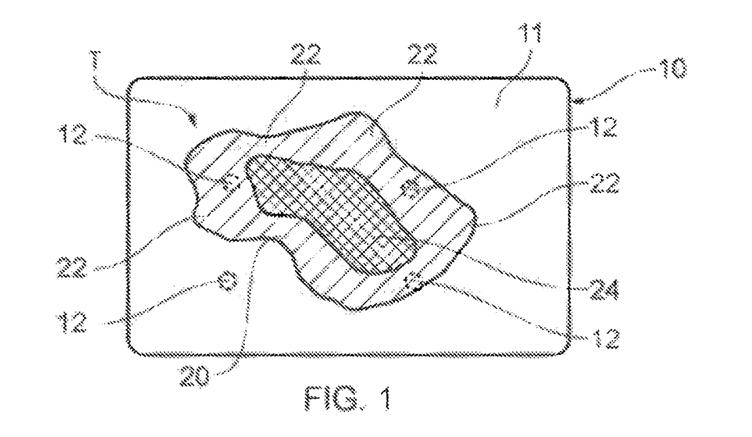
FIG. 1 shows a plan view of a tray holding a tumour transection.

Referring to FIG. 1, there is shown schematically a transection T of a cancerous tumour held in a holder 10, which in this embodiment is a tray of a size compatible with apparatus described below. The transection T is a parallel slice of the tumour which lies flat in the tray 10. The tray 10 has a base 11 which includes holding means in the form of upstanding spikes 12, which in turn hold the tumour slice in place. In the illustration, cell types at an outer region of the tumour 20, including edge portions 22, are depicted by single hatching lines, whereas cell types at an inner region 24 of the tumour are represented as having double hatching lines. It is to be appreciated that tumours generally have an ill-defined or random transition between inner region and edge portion cell types with complex heterogeneity, rather than the clear delineation illustrated schematically in FIG. 1.

Figure 2:
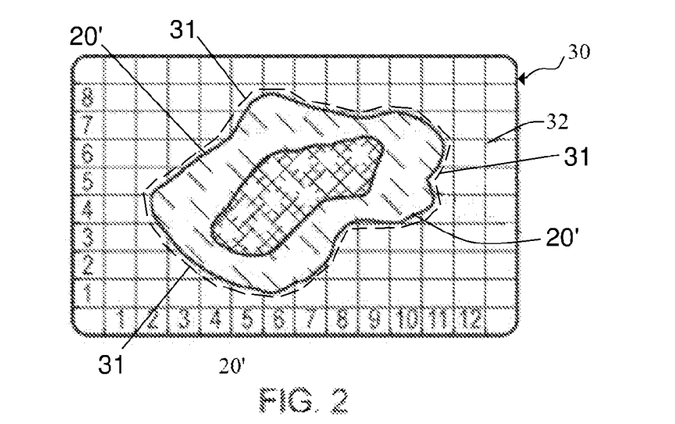
FIG. 2 shows a solid support including an imprint of the tumour shown in FIG. 1.

Referring to FIG. 2, an FTA® paper support 30 is shown onto which fits snugly into the tray 10. The holder 10 of FIG. 1 has formations i.e. tray sides, for guiding the support 30 into contact with the transection T. The support 30 may be supported by a backing layer or pad (not visible) which prevents the paper from bending in use but allows drying of the paper. The support has a contact area 31 having a pattern 32 pre-printed thereon, in this case in the form of a numbered grid. The support 30 has been fitted into the tray and pressed gently by hand onto the transection T for five seconds or more, to provide an inverted imprint 20' of the tumour 20. The imprint will consist of small but detectable amounts of biological material transferred during the pressing. In this embodiment, the FTA paper includes a dye, such as phenol red, which provides a witness mark where fluids from the tumour have wetted the paper.

Figure 3:
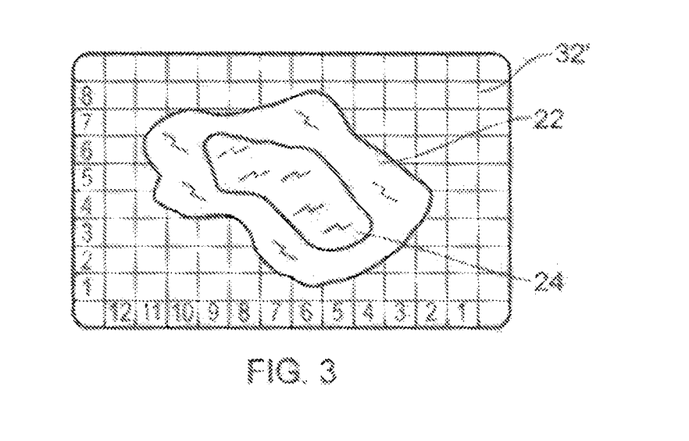
FIG. 3 shows an image of the tumour shown in FIG. 1.

Referring to FIG. 3, the tumour transection T has been stained with haematoxylin and eosin to better define the ideas of the tumour, and then photographed or otherwise imaged to provide the image shown schematically in FIG. 3. In this case a grid pattern 32' is superimposed over the image to provide the same size pattern as the grid pattern 32 printed on the support 30. The grid pattern can simply be printed onto a transparent sheet and overlaid on the transection, or it can be digitally overlaid according to known techniques. For convenience, the image shown in FIG. 3 can be reversed to match the imprint 12.

In use the following steps are performed:

1) The pathologist or researcher will transect a tumour after it is removed from a patient or animal, by cleanly cutting a cross-section through the tumour.

2) The transection is placed in the tray 10 and will be held in place by the holding means 12.

3) The support 30 will be mounted to a backing layer and applied with sufficient pressure to the exposed cut surface of the tumour, ensuring that full contact across the tumour is made for a sufficient time period (at least 5 seconds). Visual examination of the witness marks in the coloured dye on the paper will ensure that full transfer has taken place.

4) The paper will be allowed to dry.

5) Optionally, an image of the transection can be taken, possibly enhanced by surface treatments of the transection.

6) DNA from the tumour imprint can then be stored in its original spatial context on the paper support for as long as necessary.

7) Samples in the form of paper punches can be taken from any relevant area of the tumour imprint particularly from the edges portion which often includes an invasive front. The sample can be subjected to gene amplification techniques such as a Polymerase Chain reaction (PCR), reverse transcriptase PCR, quantative real time PCR, isothermal amplification, or RNA expression assays, or gene rearrangement assays, and/or other assays, for example ELISA or enzyme assays to identify the presence of certain proteins or enzymes. In preparation for PCR, nucleic acids can be eluted from the punch and added to a reverse transcriptase (RT) formulation, for example contained in a dried bead format, together with a predetermined amount of solvent in kit form. The bead may contain PCR primers designed at intron/exon boundaries to analyse gene expression in that area of the tumour. Primer sets could include, for example, EMT markers, such as E-cadherin, Snail, Slug, Twist and ZEB-2 that could be used on samples taken from the edge portion of the tumour. Samples can be taken from any area of the paper but the edge portion can be better identified by reference to the image (FIG. 3) and cross referencing the grid reference from the image onto the paper.

Embodiments of the invention provide:

1) The ability to maintain the two dimensional 'spatial map' of the tumour so that samples can be taken from well-defined areas.

2) RTG beads containing appropriate primer sets to analyse specific gene signatures that are likely to occur in precise areas of the tumour (e.g. invasive genes).

3) The requirement of only a small amount of clinical or research tumour sample to be taken.

4) Easy storage of nucleic acid for long periods of time at room temperature for later downstream analysis.

5) Ease of use for the different assays mentioned in step 7) above.

Supporting experimentation results are given below:

Examples

DNA Sample Collection and Storage

Murine tissues from c57BL/6 mice and NOS3 null mice (in a 129/B6 background) were applied to several different solid support media including FTA classic, indicating and FTA elute micro-cards, sold by Whatman Inc. The mice were euthanized and dissected to collect organs (blood, heart, brain, lung, liver, and kidney). The Organs were 'sandwiched' between two layers of the different FTA matrices described above. Pressure was applied via a sterile pipette to imbed tissues in each of the chemically-coated cellulose matrices. For tissue homogenate, approximately 5 g of tissue was processed using a plastic dounce homogenizer in a 1.5 ml microfuge tube and then subsequently applied to the appropriate FTA matrix. After application, all the samples were allowed to air-dry for 2 hours prior to storage in a sealed pouch with desiccant. In some instances, samples were stored up to 2 months before processing.

DNA Purification, Genotyping, and Quantitation

A Harris disposable micro punch (1.2 mm or 3 mm diameter) was used to excise the dried tissue samples from FTA and FTA elute micro-cards respectively in the form of punched disks. The sample disk was excised from the center of the dried sample and placed in a clean DNase free-1.5 ml micro-centrifuge tube. To extract genomic DNA from FTA and FTA elute cards standard purification procedures were followed according to Manufacturer's instructions.

Null or gene knockout NOS3 mice were identified by PCR amplification of genomic DNA with endothelial Nitric Oxide Synthases (eNOS) exon 10-specific forward primer (see sequence listing 1), eNOS Neo-specific forward primer (sequence listing 2), and eNOS exon 12-specific reverse primer (see sequence listing 3).

Target DNA's were amplified with an initial 10 min denaturation step followed by 36 cycles of 94° C. for 35 sec, 65° C. for 1 min, and 72° C. for 1 min; followed by a final extension at 72° C. for 5 min. using a MJ Research thermocycler. The resultant PCR products were visualized using an Experion capillary electrophoresis system. Mouse DNA quantification was achieved using the Primer Design genomic DNA quantification kit for mouse samples (gDNA-mo-q-DD) following manufacturer's instructions.

Figure 4A:
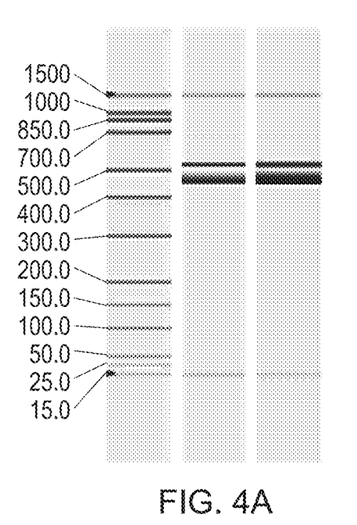
FIG. 4 shows an experimental image of amplicons.

Individual wild type (WT) and NOS null tissue samples were applied separately to different FTA cards. In some limited instances a dried sample spot was created that contained both KO and NOS null liver tissue samples. DNA was isolated from this cellular mixture and subjected to a non-optimized multiplex PCR that contained a combination of all three genotyping primers i.e. eNOS exon 10-specific forward primer, eNOS Neo-specific forward primer, and eNOS exon 12-specific reverse primer. A representative gel is shown in FIG. 4a indicating the simultaneous amplification of both products from a mixed tissue source in a single PCR reaction.

Genotype Discrimination Via PCR Analysis

In order to exemplify the ability to differentiate genotypic variants from DNA stored on FTA matrices, PCR amplification of a region was carried out on WT and transgenic (NOS3 null, gene knock-out) mice.

Figure 4B:
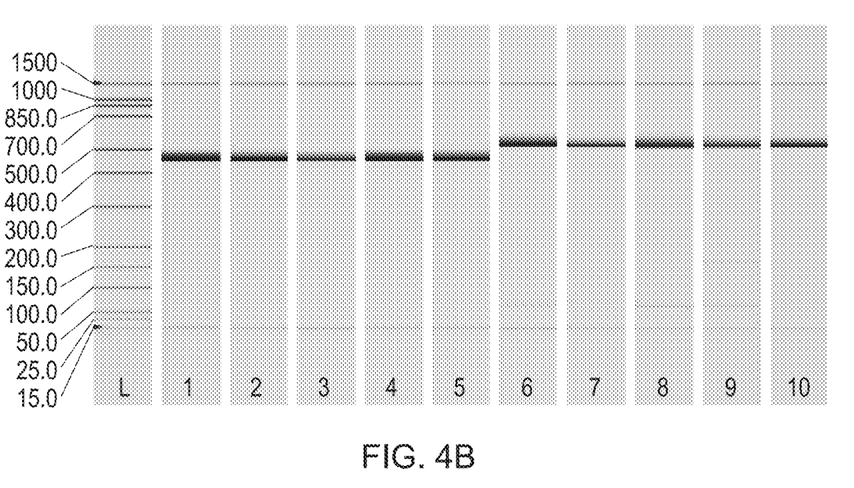

FIG. 4b and Table 1 (below) show the DNA amplification products derived from both the WT and NOS3 null gene knock-out mice respectively. Results indicate that for both sample sources, the correctly sized DNA amplicons were produced from DNA isolated from all organ/tissue sources applied to the FTA matrix. Similar results were presented for the FTA elute matrix (data not shown). These data indicate that 1.2 mm Harris micro-punches can excise sufficient DNA from tissue stored on FTA and FTA micro-cards to differentiate two genetic variants.

In FIG. 4b banded PCR amplicons are shown, associated with the NOS locus using DNA as an amplification template isolated from tissues from FTA cards. Lanes 1-5 are DNA isolated from WT mouse tissue (Heart, Liver, Brain, Lung, and Kidney respectively). Lanes 6-10 are DNA amplified from NOS mouse tissues (Heart, Liver, Brain, Lung, and Kidney respectively). Equivalent results have been found with FTA elute and indicating FTA.

TABLE 1

| DNA type | DNA Source | FTA Microcards | FTA Indicating | FTA Elute Microcards | FTA classic cards |
|---|---|---|---|---|---|
| Wild Type Tissue DNA | Blood | + | ND | ND | ND |
| | Heart | ND | + | + | + |
| | Liver | ND | + | + | + |
| | Brain | ND | + | + | + |
| | Lung | ND | + | + | + |
| | Kidney | ND | + | + | + |
| Knock Out Tissue DNA | Blood | + | ND | ND | ND |
| | Heart | ND | + | + | + |
| | Liver | ND | + | + | + |
| | Brain | ND | + | + | + |
| | Lung | ND | + | + | + |
| | Kidney | ND | + | + | + |

In Table 1 the successful amplification of DNA isolated from tissues stored on various FTA papers is recorded. DNA was isolated from a 1.2 mm punch. '+' signifies the presence of amplicons, and ND represents not determined.

RNA Purification and Quantitation

Tissue samples were applied to FTA cards as described above. FTA sample punches were excised and the RNA isolated using the GE Healthcare illustra RNAspin kit as described below. RNA quantitation was performed on an ABI 7900 real time PCR system utilizing the commercially-available mRNA quantification kits as detailed in Table 2.

Using a Harris 3 mm disposable micro punch, a punch was excised from the center of the dried sample spot and place in a clean RNase-free 1.5 ml micro-centrifuge tube. The illustra buffer RA1 (350 µl) was combined with 3.5 µl β-mercaptoethanol and the solution was added to the disc. The disc was homogenized using a 20 gauge needle. The resultant homogenate was transferred to the RNAspin Mini filter column for subsequent removal of residual material. The column was centrifuged for 1 min at 11,000×g. and the RNAspin Mini Filter discarded. The homogenized lysate contains the RNA and this filtrate was transferred to a new RNase-free 1.5 ml micro-centrifuge tube.

Ethanol (70%; 350 µl) was added to the homogenized lysate and mixed by vortexing for 2×5 sec pulses. For each preparation, the lysate was pipette up-and-down 2-3 times, and applied to an RNA Mini-spin column placed in a 2 ml micro-centrifuge tube. The tubes were centrifuged for 30 sec at 8000×g and the flow through discarded. The RNA spin column was transferred to a new collection tube.

The illustra MDB buffer (350 µl) was added and the tube centrifuged at 11 000×g for 1 min. Once again the flow-through was discarded and the column returned to the collection tube. A DNase reaction mixture was prepared according to manufacturer's instructions and was added to the surface of the filter contained within the RNAspin column. This DNAse incubation was performed at room temperature for 15 min.

The wash buffer RA2 (200 µl) was applied to the RNA Mini-spin column and the column was centrifuged for 1 min at 11 000×g. Once again the flow-through was discarded and the column returned to the collection tube.

Buffer RA3 600 µl was applied to the RNA Mini-spin column and the column centrifuge for 1 min at 11 000×g the flow-through was discarded and the column returned to the collection tube. An addition column wash with buffer RA3 (250 µl) was also performed. In order to dry the membrane completely, the column was centrifuged for 2 min at 11 000×g and the column finally placed into a nuclease-free 1.5 ml micro-centrifuge tube.

RNase-free water (40 μl) was applied to the column and the column centrifuged at 11 000×g for 1 min. The purified RNA was either used immediately in downstream applications or stored at −80° C. until used.

To determine the integrity of RNA from multiple tissues after prolonged storage, real-time reverse transcription polymerase chain reaction (RT-PCR) was carried out on RNA isolated from mouse tissue samples stored on FTA and FTA elute. Cards were stored in the presence of a desiccant for 2 months. mRNA quantification was accomplished according to manufacturer's instructions using either i) the ABI Taqman rodent GAPDH control kit (part #4308313), ii) the Invitrogen real-time LUX mRNA primer sets for murine HPRT, GAPDH, and Beta-Actin genes (cat. 105M-02, 100M-02, and 101M-02 respectively) or iii) tissue specific gene primer sets from Applied Bio-systems (see Table 2 for details).

TABLE 2

Tissue specific genes tested for relative RNA quantitation.

| Catalog number | Gene | Organ Specificity |
| --- | --- | --- |
| Mm00475834_m1 | Alkaline Phosphatase | Liver, bone, kidney |
| Mm01266402_m1 | Myelin Basic Protein | Brain |
| Mm01313844_mH | Myh6 | Smooth muscle (Heart, lungs) |
| Mm00437306_m1 | VEGF | Lungs |

Figure 5:
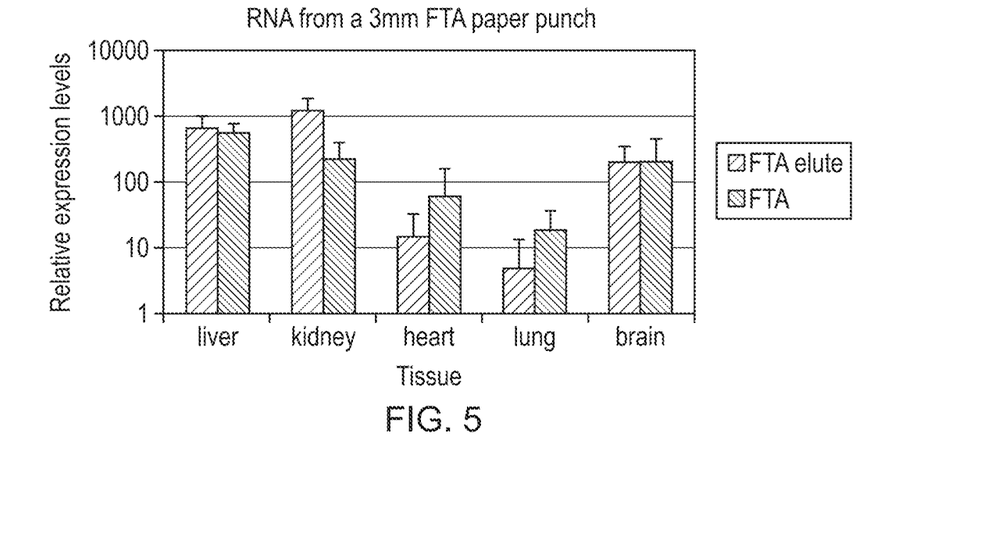
FIGS. 5 to 12 show experimental data in graphical form.

FIG. 5 shows the relative expression levels of GADPH from several tissue sources using the ABI Taqman rodent GAPDH control kit. RNA levels derived from the FTA cards were determined by comparison to known values generated from a quantification titration curve from mouse RNA standard samples. Comparable GAPDH RNA levels were detected from RNA isolated from both paper types. This indicates that both FTA and FTA elute paper matrices are suitable solid support matrices for the short-medium term storage of RNA from tissues. Murine RNA from tissues derived from C57Bl/6 mice was isolated from a single 3 mm punch of FTA and FTA Elute. RNA was purified using illustra RNA Mini-spin kit.

Figure 6:
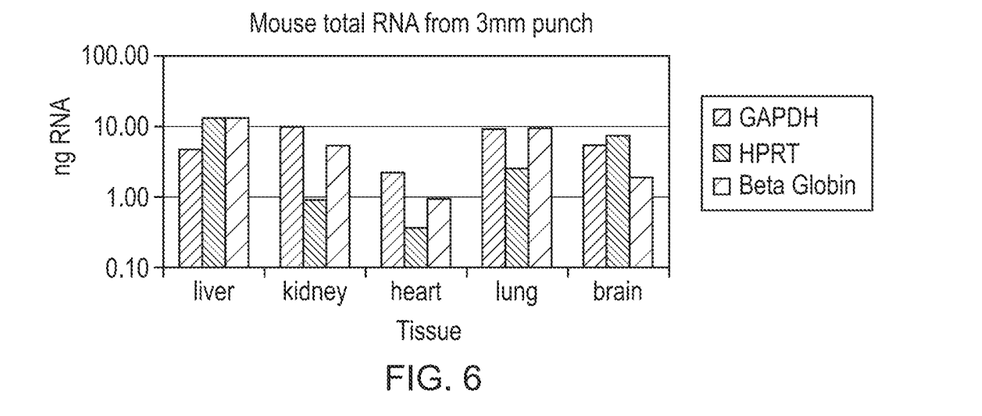

Absolute quantitation of murine mRNA encoding HPRT, GAPDH and Beta-Actin was carried out with the appropriate Invitrogen real-time LUX primer sets. RNA levels derived from the FTA cards were determined by comparison to known values generated from a quantification titration curve from mouse RNA standard samples. Data associated with the isolation of RNA from FTA cards is described in FIG. 6 and demonstrate that FTA cards are able to support the storage of RNA from numerous tissue types. Similar observations were apparent for RNA stored on FTA elute.

Figure 7:
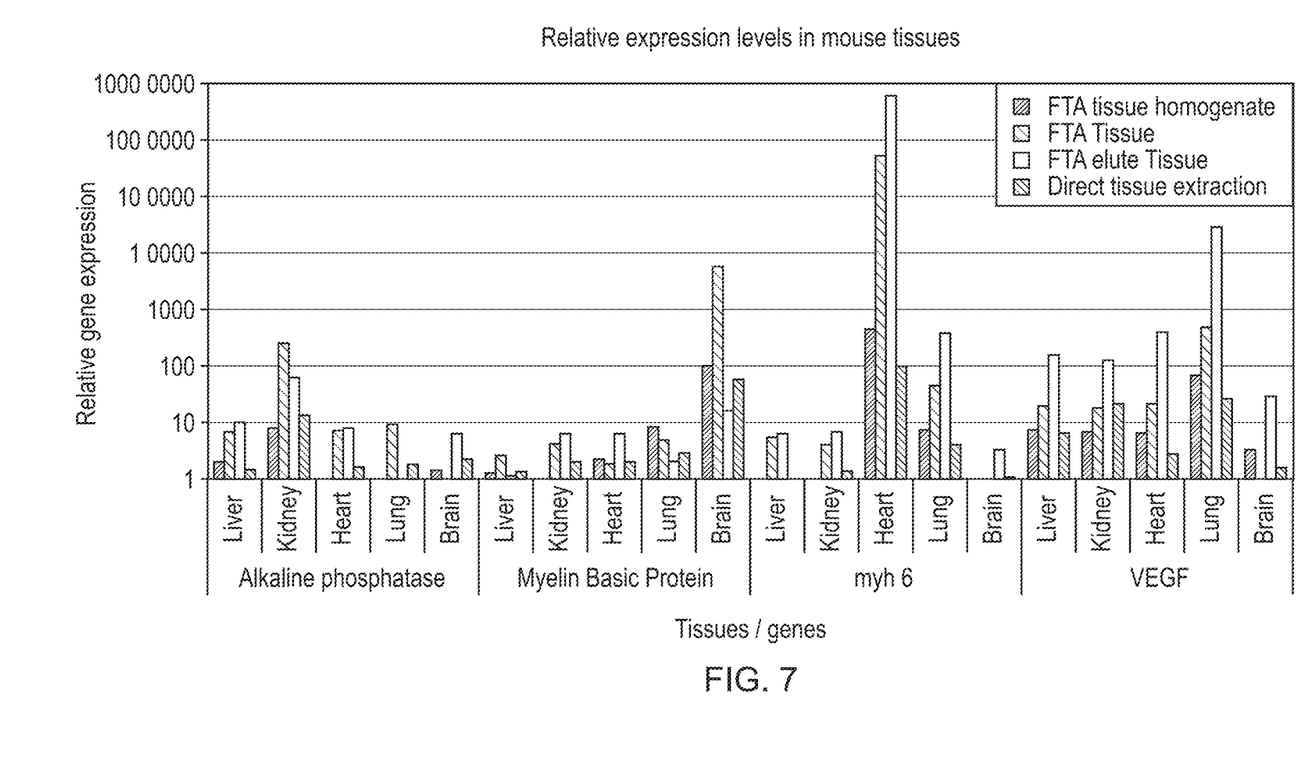

To investigate the mRNA levels in the FTA and FTA elute archived tissue samples, the relative expression levels of the mRNA described in Table 2 was determined using with real-time tissue specific RT-PCR probes (see FIG. 7). The GAPDH mRNA transcript was used to standardize the total RNA levels in each sample. Additional controls involved homogenized tissue that had been applied to FTA cards and the use of freshly isolated RNA derived from the illustra RNA Mini-spin kit.

Results show elevated mRNA levels for; Alkaline Phosphatase in Kidney; myelin basic protein in brain; Myh6 message in heart and lung; and elevated VEGF mRNA levels from lung tissue sources compared to the other mRNAs. This trend was apparent irrespective of the sample type i.e. tissue stored on directly on FTA, homogenized prior to storage or freshly isolated RNA. These data agree with predicted expression patterns and levels of these mRNAs from these tissue sources. These data demonstrate that both FTA and FTA elute are able to preserve mRNA levels from all tissue sources irrespective of the sample type i.e. card-based or fresh formats.

RNA Analysis from Tumours Using Gene Target Prepared from a Solid Support

Two dimensional (2D) tumour mapping could be used to analyse molecular markers of tumour invasion such as those involved in Epithelial-to-Mesenchymal Transistion (EMT) which primarily occurs at the tumour's edge. Table 3 below describes examples of appropriate gene markers that could be used to determine the invasiveness of a tumour.

TABLE 3

| Gene Name | Gene Symbol | Role in Cancer | Reference |
| --- | --- | --- | --- |
| E-Cadherin | CDH1 | Encodes a cell-cell adhesion glycoprotein. Down-regulation in cancer results in loss intracellular adhesion, promoting cell invasion. | Hazan RB et al. 2004. |
| Snail family zinc finger 1 | SNAI1 | EMT inducer. Transcriptional repressor of E-cadherin. Modulates expression of genes involved in invasion. Up-regulation in cancer promotes cell invasion. | Cano, A et al. (2007). |
| Snail family zinc finger 2 | SNAI2, SLUG | EMT inducer. Transcriptional repressor of E-cadherin. Modulates expression of genes involved in invasion. Up-regulation in cancer promotes cell invasion. | Bolos, V et al. (2003). |
| Zinc finger E-box binding homeobox 1 | ZEB1 | EMT inducer. Transcriptional repressor of E-cadherin. Up-regulation in cancer promotes cell invasion. | Eger A et al. (2005). |
| Zinc finger E-box binding homeobox 2 | ZEB2 | EMT inducer. Transcriptional repressor of E-cadherin. Up-regulation in cancer promotes cell invasion. | Comijn J et al. (2001). |

TABLE 3-continued

| Gene Name | Gene Symbol | Role in Cancer | Reference |
|---|---|---|---|
| Twist family bHLH transcription factor 1 | TWIST1 | EMT inducer. Transcriptional repressor of E-cadherin. Up-regulation in cancer promotes cell invasion. | Yang J et al. (2004). |
| Non-metastatic cells 1 | NME1 | Inhibits cell motility and metastases. Down-regulation in cancer promotes cell invasion. | Horak, C. E et al. (2007). |
| Tissue inhibitor of metalloproteinase 1&3 | TIMP1&3 | Inhibit matrix metalloproteinases which promote invasion by the breakdown the extracellular matrix. Down-regulation of TIMPs in cancer promotes cell invasion. | Bloomston, M et al. (2002). Zhang, L et al (2010). |

References provided in the table above:

Horak, C. E., J. H. Lee, e t al. (20 07). "N m 2 3-H 1 suppresses tumor cell motility by down-regulating the lysophosphatidic acid receptor EDG2." Cancer Res 67(15): 7 23 8-7246.

Bloomston, M., A. Shafii, et al. (2002). "TIMP-1 overexpression in pancreatic cancer attenuates tumor growth, decreases implantation and metastasis, and inhibits angiogenesis." J Surg Res 102(1): 39-44

Zhang, L., L. Zhao, et al. (2010) "Inhibition of tumor growth and induction of apoptosis in prostate cancer cell lines by overexpression of tissue inhibitor of matrix metalloproteinase-3." Cancer Gene Ther. 17(3):171-9.

Cano A, Perez-Moreno M A, Rodrigo I, et al. (2000). "The transcription factor snail controls epithelial-mesenchymal transitions by repressing E-cadherin expression." Nat Cell Biol 2:76-83.

Bolos V, Peinado H, Perez-Moreno M A, et al. (2003). "The transcription factor Slug represses E-cadherin expression and induces epithelial to mesenchymal transitions: a comparison with Snail and E47 repressors." J Cell Sci 116: 499-511.

Comijn J, Berx G, Vermassen P, et al. (2001) "The two-handed E box binding zinc finger protein SIP1 downregulates Ecadherin and induces invasion." Mol Cell 7:1267-78.

Eger A, Aigner K, Sonderegger S, et al. (2005) "DEF1 is a transcriptional repressor of E-cadherin and regulates epithelial plasticity in breast cancer cells." Oncogene 24:2375-85.

Yang J, Mani S A, Donaher J L, et al. (2004) "Twist, a master regulator of morphogenesis, plays an essential role in tumor metastasis." Cell 117:927-39.

Hazan R B, Qiao R, Keren R, Badano I, Suyama K (2004) "Cadherin switch in tumor progression." Ann N Y Acad Sci 1014:155-63.

Enzyme Detection from Cells or Enzymes Transferred to Solid Supports

Protein and enzyme testing was carried out with fully configured DNase and RNase Contamination Kits (DNase & RNase Alert QC Systems, catalogue codes AM1970 & AM1966, Life Technologies) according to the manufacturer's instructions.

In a first series of experiments, 0.125-0.5 U of DNase was applied to FTA and 903 brand papers sold by Whatman Inc in 10 µl volumes. DNAse and RNase activity was measured as outlined below.

In a second series of experiments, 1.2 mm punches were taken from $10^6$ human embryonic stem cells (GE Healthcare; cell line ref: WCB307 GEHC 28) which had been applied to FTA and 903 papers in 10 µl volumes as above. DNAse and RNase activity was measured as outlined below.

In a third series of experiments, 1.2 mm punches were taken from $10^6$ human embryonic stem cells (GE Healthcare; cell line ref: WCB307 GEHC 28) containing either 0.5 U of DNase or 10 µU of RNase added to these cells which had been applied to FTA and 903 papers in 10 µl volumes.

Detection of DNase activity was carried out as follows using a cleavable fluorescent-labelled DNase substrate. Each punch was ejected into separate wells of 96-well plates. Lyophilized DNase Alert Substrate was dissolved in TE buffer (1 ml) and dispensed (10 µl) into the test wells of the 96-well plate. 10× DNase Alert Buffer (10 µl) and nuclease-free water (80 µl) was added and the test solution (100 µl) incubated for 60 minutes at 37° C. The DNase Alert QC System Substrate is a modified DNA oligonucleotide that emits a pink fluorescence when cleaved by DNase. For this assay, fluorescence was measured on a Tecan Ultra (excitation/emission 535/595 nm using medium gain). Solutions containing DNase activity produced a pink fluorescence, whereas solutions without DNase activity did not fluoresce. Thus, higher levels of DNase corresponded to an increase in the amount of light output. Negative controls consisted of nuclease-free water (80 µl) in place of sample. DNAase activity can be detected and quantified in a rate dependent manner using the 903 or FTA papers.

Figure 8:
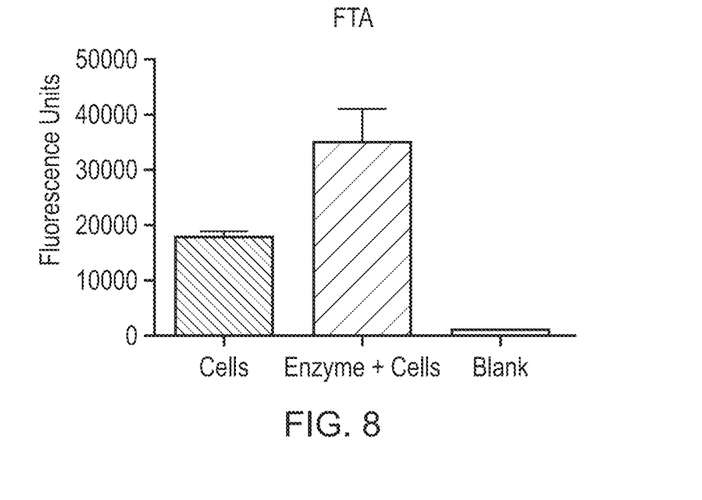
Figure 9:
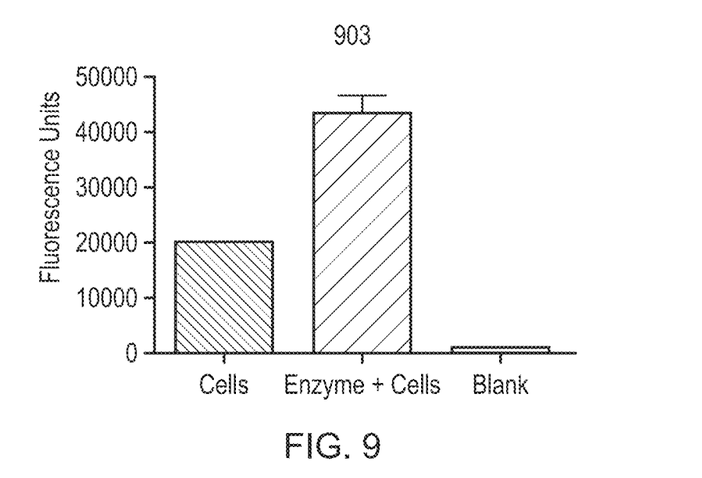

FIGS. 8 and 9 illustrate the relative fluorescence of samples stored on FTA paper and 903 paper using the methodology mentioned immediately above.

Detection of RNase was carried out as follows using a cleavable fluorescent-labelled RNase substrate. Each punch was ejected into separate wells of 96-well plates. Lyophilized RNase Alert Substrate was dissolved in TE buffer (1 ml) and dispensed (10 µl) into the test wells of the 96-well plate. 10× RNase Alert Buffer (10 µl) and nuclease-free water (80 µl) was added and the test solution (100 µl) incubated for 60 minutes at 37° C. The RNase Alert QC System Substrate is a modified RNA oligonucleotide that emits a green fluorescence when cleaved by RNase. For this assay, fluorescence was measured on a Tecan Ultra (excitation/emission 485/535 nm using medium gain). Solutions containing RNase produced a green fluorescence, whereas solutions without RNase activity did not fluoresce. Thus, higher levels of RNase corresponded to an increase in the amount of light output. Negative controls consisted of nuclease-free water (80 µl) in place of sample. RNAase activity can be detected and quantified in a rate dependent manner using the 903 or FTA papers.

Figure 10:
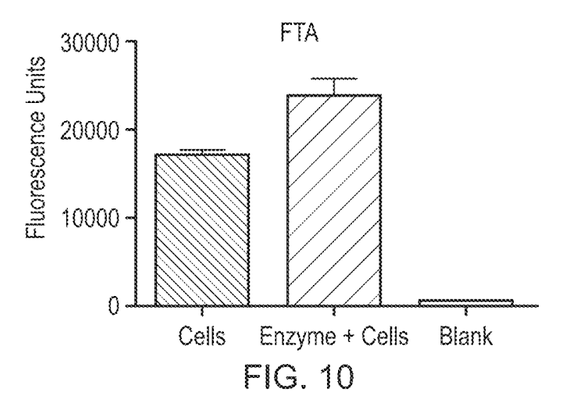
Figure 11:
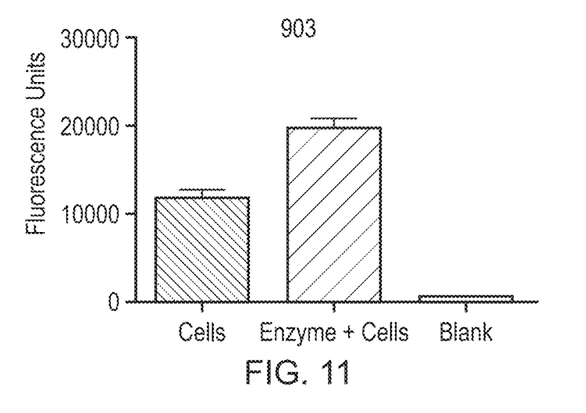

FIGS. 10 and 11 illustrate the relative fluorescence of samples stored on FTA paper and 903 paper, using the methodology mentioned immediately above.

Detection of a Model Protein Applied to the Solid Supports

Recombinant IL-2±carrier (R & D Systems; Cat. 202-IL-CF-10 µg; lot AE4309112 and Cat. 202-IL-10 µg; lot AE4309081 respectively) was dissolved in either Dulbecco's PBS without calcium and magnesium (PAA; Cat. H15-002, lot H00208-0673), EDTA-anti-coagulated human, rabbit or horse blood (TCS Biosciences) at 50 pg or 100 pg/µl.

Aliquots (1 µl containing 0.5 (B) or 100 (A) pg of IL-2; (See FIG. 12) were applied to the following GE Healthcare filter papers; 903 Neonatal STD card, Cat. 10538069, lot 6833909 W082; DMPK-A card, Cat. WB129241, lot FT6847509; DMPK-B card, Cat. WB129242, Lot FE6847609 and DMPK-C card, Cat. WB129243, Lot FE6847009. Samples were allowed to dry overnight at ambient temperature and humidity.

Punches (3 mm diameter) were extracted from each paper type using the appropriately sized Harris Uni-core punch (Sigma, Cat.Z708860-25ea, lot 3110). Single punches were placed into individual wells of the IL-2 microplate derived from the Human IL-2 Quantikine ELISA (R & D Systems, Cat. D0250, lot 273275). These plates are coated with a mouse monoclonal antibody against IL-2. The IL-2 protein was eluted from the paper punch using the assay buffer (100 µl) supplied with the Quantikine kit. All subsequent steps were performed according to the instructions supplied with the Quantikine kit using a "paper in" method (paper punches are placed directly into the assay buffer and the analyte eluted directly in situ). On completion of the assay the optical density of the microplate was monitored at 450 nm using a Thermo Electron Corporation, Multiskan Ascent. The recovery of IL-2 was determined by comparing values to a standard curve of known IL-2 concentrations. A fresh IL-2 standard curve was prepared for each individual experiment.

Figure 12:
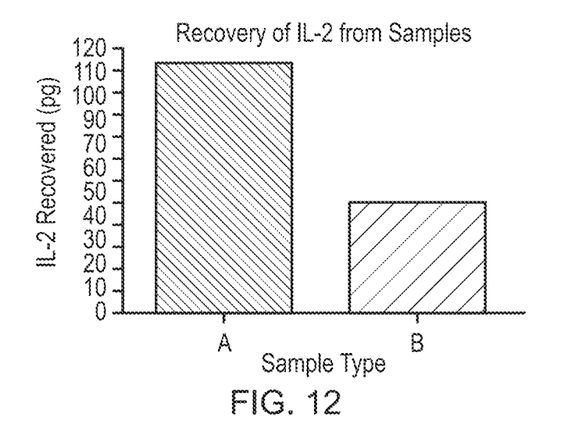

The recovery rate of a model protein (interleukin 2 IL-2) from DMPK-C Cards for each of the samples A and B is illustrated in FIG. 12.

Although one embodiment has been described and illustrated, it will be apparent to the skilled addressee that additions, omissions and modifications are possible to those embodiments without departing from the scope of the invention claimed. For example, although the specific example shown in FIGS. 1 2 and 3 has been described as employing a solid support 30 sold under the FTA brand, the experimental data shown above illustrates that the technique can be used with other solid supports, as for example detailed below.

Herein FTA (including FTA microcards, FTA indicating, and FTA claissic) is a cellulous fibre paper treated with stabilising chemicals, for example a weak base, a chelating agent and an anionic surfactant, whereby the support surface is impregnated with the stabilisation chemicals. In this way the biological sample materials can be stored on the apparatus for many months or even years, thereby allowing time for transportation of the apparatus, if needed, to a laboratory, at an ambient temperature, and adequate recovery is then possible, simply by dissolving the stored sample and reagents. FTA Elute herein describes similar paper but coated with a chaotropic agent such as guanidinium thiocyanate, to allow direct assay of biological material, without the need to remove chemicals employed with FTA paper. Herein 903 describes uncoated cellulose fibre paper.

It is possible to use other solid supports such as a glass fibre/microfibre material or a porous polymer, for example porous membrane material such as polyester, polyether sulfone (PES), polyamide (Nylon), polypropylene, polytetrafluoroethylene (PTFE), polycarbonate, cellulose nitrate, cellulose acetate or aluminium oxide.

The solid supports described above are intended to be used in a generally flat configuration, but in the alternative, may for example be used on a roll and rolled of the tumour/mass surface.

Further, whilst the specific example refers to tumour transections, other biological masses can be profiled according to the same techniques.

The invention claimed is:

1. An apparatus for capturing a spatial profile of biological material from at least a portion of a biological mass, the apparatus comprising:
 a biological mass tray configured to hold the biological mass and to hold a solid support;
 chemicals; and
 the solid support, the solid support defining a support surface having a contact area configured to contact at least the portion of the mass to retain a two dimensional imprint of the portion of the biological mass, the solid support further including a preformed reference grid at least at said contact area,
 wherein the support surface is impregnated with the chemicals, and
 wherein the chemicals include a weak base, a chelating agent, an anionic surfactant, or a chaotropic agent.

2. The apparatus as claimed in claim 1, wherein the solid support is fibrous.

3. The apparatus as claimed in claim 1, wherein the solid support comprises a porous polymer.

4. The apparatus as claimed in claim 1, wherein the biological mass tray has means for holding the biological mass in a static position relative to the tray.

5. The apparatus as claimed in claim 1, further including an imaging device for capturing an image of the biological mass and for superimposing a grid of the same or similar proportions to the reference grid on the support.

6. The apparatus as claimed in claim 1, further comprising the biological mass, wherein the biological mass comprises a tumor.

7. The apparatus as claimed in claim 2, wherein the solid support comprises a cellulose or glass.

8. The apparatus as claimed in claim 3, wherein the porous polymer comprises polyester, polyether sulfone (PES), polyamide (Nylon), polypropylene, polytetrafluoroethylene (PTFE), polycarbonate, cellulose nitrate, or cellulose acetate.

* * * * *